(12) United States Patent
Marathakis et al.

(10) Patent No.: US 9,724,086 B2
(45) Date of Patent: Aug. 8, 2017

(54) MENISCUS HORN RELOCATION DEVICE AND METHOD

(71) Applicant: Empire Technology Development LLC, Wilmington, DE (US)

(72) Inventors: Phillip Marathakis, Emu Plains (AU); Deniz Ozdil, Auburn (AU); Gregory James Roger, Crows Nest (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 113 days.

(21) Appl. No.: 14/579,994

(22) Filed: Dec. 22, 2014

(65) Prior Publication Data

US 2016/0174962 A1  Jun. 23, 2016

(51) Int. Cl.
*A61B 17/04* (2006.01)
*A61B 17/06* (2006.01)
*A61B 17/064* (2006.01)
*A61B 17/00* (2006.01)

(52) U.S. Cl.
CPC .... *A61B 17/0401* (2013.01); *A61B 17/06004* (2013.01); *A61B 17/06166* (2013.01); *A61B 17/0642* (2013.01); *A61B 2017/00898* (2013.01); *A61B 2017/0417* (2013.01); *A61B 2017/0477* (2013.01); *A61B 2017/06009* (2013.01)

(58) Field of Classification Search
CPC ........ A61B 17/06166; A61B 17/06004; A61B 17/0401; A61B 17/0642; A61B 17/0417; A61B 17/06009; A61B 17/04
See application file for complete search history.

(56) References Cited

U.S. PATENT DOCUMENTS

| | | | |
|---|---|---|---|
| 5,931,840 | A | 8/1999 | Goble et al. |
| 6,699,252 | B2 | 3/2004 | Farr, II et al. |
| 7,871,440 | B2 | 1/2011 | Schwartz et al. |
| 8,152,846 | B2 | 4/2012 | Steiner et al. |
| 8,221,454 | B2 | 7/2012 | Schaffhausen |
| 8,357,203 | B2 | 1/2013 | White et al. |

(Continued)

FOREIGN PATENT DOCUMENTS

| | | |
|---|---|---|
| CN | 202665606 U | 1/2013 |
| EP | 0702933 A1 | 3/1996 |

(Continued)

OTHER PUBLICATIONS

"Comprehensive Solutions for Forefoot and Midfoot Surgery the Mini TightRope System," Arthrex Inc., pp. 1-13 (2008).

(Continued)

*Primary Examiner* — Victor Nguyen
(74) *Attorney, Agent, or Firm* — Maschoff Brennan (57) ABSTRACT

Devices, systems, and methods are disclosed for relocating a meniscus horn in a knee. The invention may be deployed during an arthroscopic procedure to apply external forces to a meniscus horn to pull the meniscus into a load bearing area of the knee, which may reduce contact stresses on articular cartilage in the knee and thereby ameliorate pain associated with an osteoarthritic joint. In one embodiment, the system includes a guide needle, suture thread, plug, elongate member, and bone anchor.

23 Claims, 11 Drawing Sheets

(56) References Cited

U.S. PATENT DOCUMENTS

| | | |
|---|---|---|
| 2006/0052787 A1 | 3/2006 | Re et al. |
| 2007/0191957 A1 | 8/2007 | Anderson et al. |
| 2008/0275431 A1 | 11/2008 | Stone et al. |
| 2011/0112556 A1 | 5/2011 | Saliman et al. |
| 2012/0143215 A1* | 6/2012 | Corrao et al. ..... A61B 17/0057 606/139 |
| 2012/0158053 A1 | 6/2012 | Paulos |
| 2012/0179254 A1 | 7/2012 | Saliman |
| 2013/0226300 A1* | 8/2013 | Chataigner et al. .... A61F 2/442 623/17.16 |

FOREIGN PATENT DOCUMENTS

| | | |
|---|---|---|
| JP | 2000210298 A | 8/2000 |
| WO | 2013055390 A1 | 4/2013 |

OTHER PUBLICATIONS

Yu, G.V., and Chang, T.J., "Soft Tissue Anchors," accessed at http://www.podiatryinstitute.com/pdfs/Update_1992/1992_25.pdf , accessed on Jul. 10, 2014, pp. 120-125.

* cited by examiner

MENISCUS HORN RELOCATION DEVICE AND METHOD

BACKGROUND

Joint replacement therapy for osteoarthritic knees is a serious procedure that is not suitable for a large number of patients with painful knees, where age and condition severity do not meet the recommended criteria for procedure. This leaves a great proportion of sufferers in pain and with debilitated lifestyles until joint replacement therapy can no longer be avoided. There remains a need for solutions that can delay the joint replacement procedure by restoring a degree of painless, or less painful, functionality to the knee joint.

SUMMARY

In one embodiment, a system for relocating a meniscus horn is disclosed. The system may include: a guide needle for puncturing the tissue of a meniscus, where the guide needle includes a distal point and a proximal eyelet, where a longitudinal axis is defined between the distal point and the proximal eyelet; an elongate member including a distal eyelet, a body portion including a plurality of gripping arms, and a proximal end region, where a longitudinal axis is defined between the distal eyelet and the proximal end region; a suture thread including a first end threaded through the proximal eyelet of the guide needle and a second end threaded through the distal eyelet of the elongate member, wherein the first and second ends of the suture thread are coupled to opposing ends of a plug, thereby forming a closed loop that flexibly couples the guide needle to the elongate member; and a bone anchor for anchoring the proximal end region of the elongate member to a bony structure in the knee joint.

In one embodiment of the invention, a method for relocating a meniscus is disclosed. The method may include: providing a system for relocating a meniscus horn, the system including a guide needle for puncturing the tissue of a meniscus, wherein the guide needle includes a distal point and a proximal eyelet, wherein a longitudinal axis is defined between the distal point and the proximal eyelet; an elongate member including a distal eyelet, a body portion including a plurality of gripping arms, and a proximal end region, wherein a longitudinal axis is defined between the distal eyelet and the proximal end region; and a suture thread including a first end threaded through the proximal eyelet of the guide needle and a second end threaded through the distal eyelet of the elongate member, wherein the first and second ends of the suture thread are coupled to opposing ends of a plug, thereby forming a closed loop that flexibly couples the guide needle to the elongate member; inserting the distal point of the guide needle into the meniscus at a location along a posterior surface of the meniscus. The guide needle is advanced laterally through the meniscus, the meniscus capsule, and the skin, until the distal eyelet of the elongate member passes through the meniscus capsule. The suture thread loop is cut distal to the proximal eyelet of the guide needle, and the free end of the suture plug is pulled through the distal eyelet of the elongate member thereby lodging the plug within the distal eyelet. The proximal end region of the elongate member is pulled away from the posterior-lateral surface of the meniscus until the plug lodged in the distal eyelet engages the meniscus capsule. The proximal end region of the elongate member is pulled until the meniscus is repositioned to a desired location within the joint. The proximal end region of the elongate member may then be anchored to a bone using the bone anchor, thereby securing the meniscus at the desired location.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Provided herein are devices, systems, and methods for the relocation of a meniscus horn within the joint cavity of a knee. These devices, systems, and methods may be employed during an arthroscopic procedure to apply external forces to a meniscus horn and thereby pull the meniscus into a load bearing area of the knee. Thus, the disclosed devices, systems and methods may reduce contact stresses on articular cartilage in the knee, and thereby ameliorate pain associated with an osteoarthritic joint.

Figure 1:
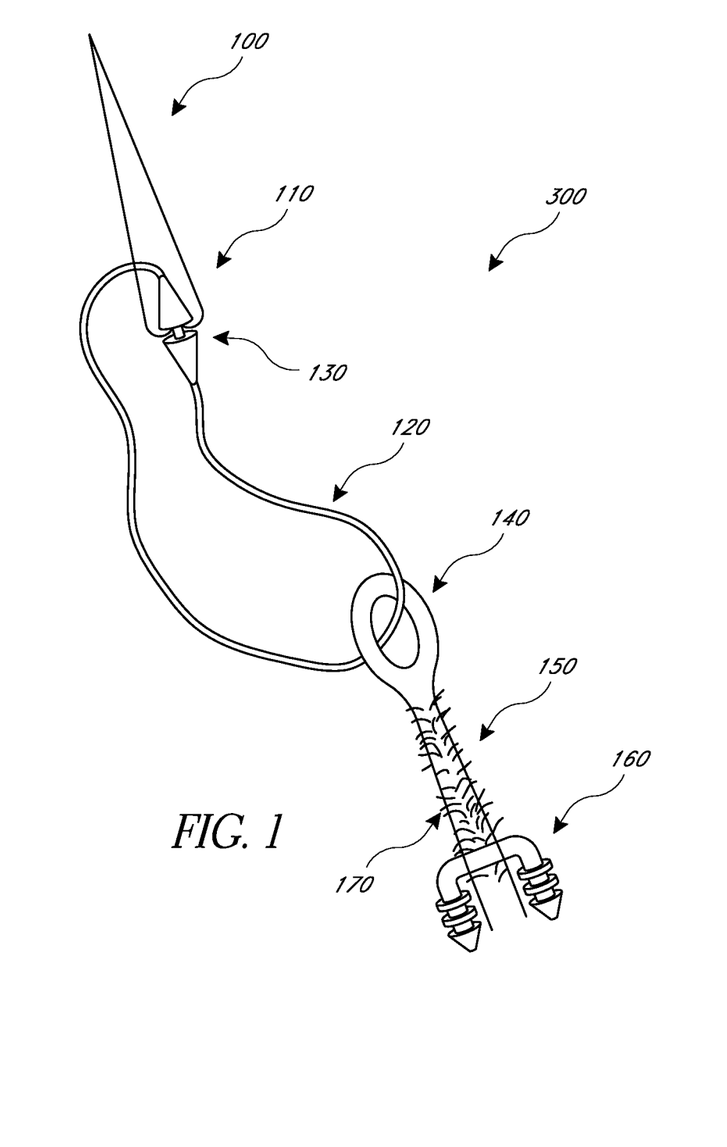
FIG. 1 illustrates one embodiment of the disclosed system.

With reference to FIG. 1, there is shown a meniscus horn relocation system 300. The meniscus horn relocation system 300 includes a guide needle 100 with proximal eyelet 110, a suture thread 120 that is attached in the illustrated embodiment at both ends to a plug 130, an elongate member 150 with distal eyelet 140, and a bone anchor 160. In some embodiments, as illustrated, the elongate member 150 may include a plurality of hair-like fibers 170.

Figure 2A:
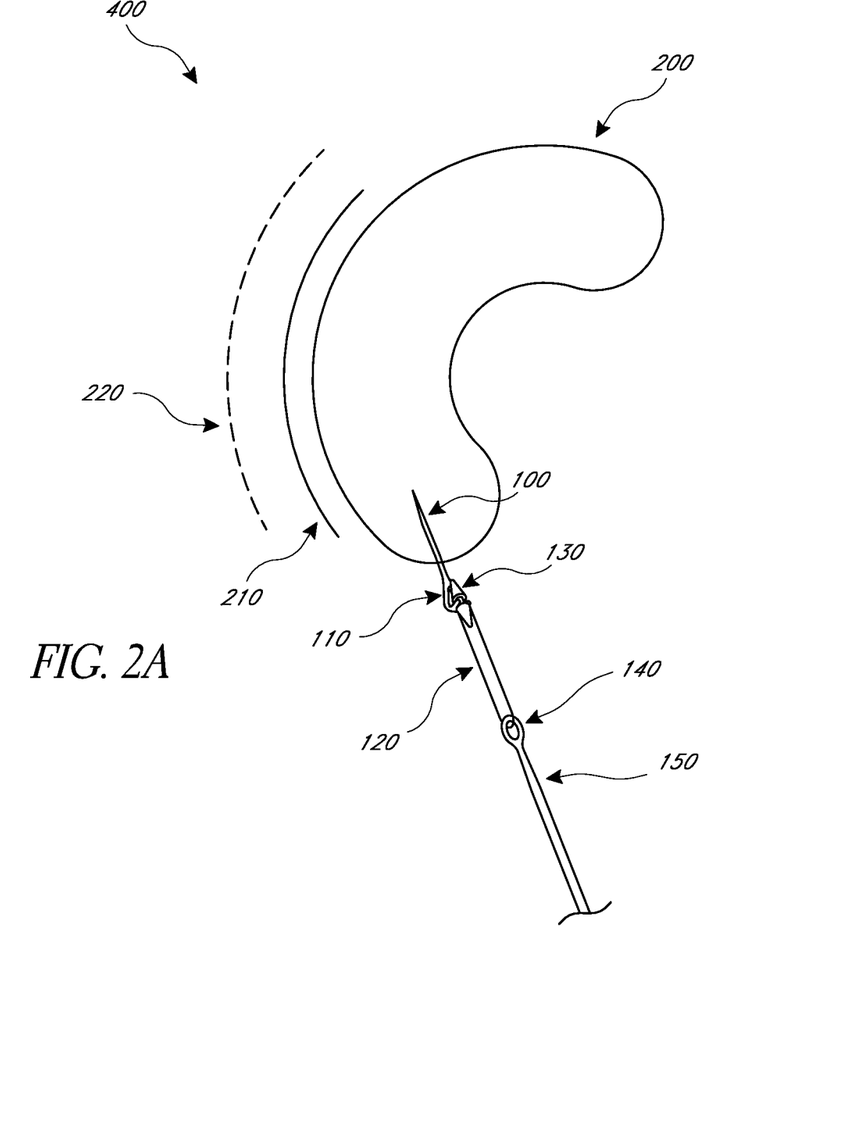
FIG. 2A illustrates a step in a meniscus relocation procedure whereby the guide needle enters the meniscus obliquely at the posterior meniscal horn.

With reference to FIG. 2A, there is shown a cross-sectional, plan view of a knee 400 showing skin 220, capsule 210, and meniscus horn 200 with guide needle 100 arthroscopically inserted into meniscus horn 200 with plug 130 attached in the proximal eyelet 110. Guide needle 100 is attached to elongate member 150 with distal eyelet 140 by suture thread 120.

Figure 2B:
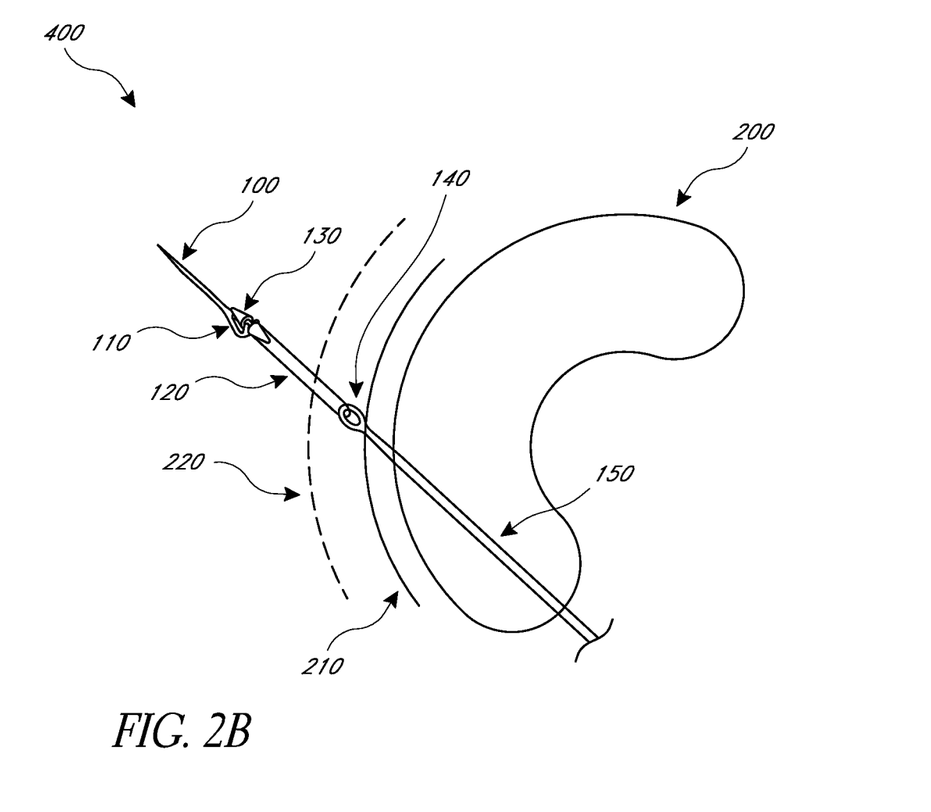
FIG. 2B illustrates a step in a meniscus relocation procedure whereby the guide needle passes through the skin and the distal eyelet of the elongate member passes through the meniscus capsule.

With reference to FIG. 2B, there is shown a cross-sectional, plan view of a knee 400 showing skin 220, capsule 210, and meniscus horn 200 with guide needle 100 arthroscopically inserted into meniscus horn 200 with plug 130 attached in the proximal eyelet 110. Guide needle 100 is passed through meniscus horn 200, capsule 210, and skin 220 until distal eyelet 140 of elongate member 150 passes through capsule 210. Guide needle 100 is attached to elongate member 150 with distal eyelet 140 by suture thread 120.

Figure 3A:
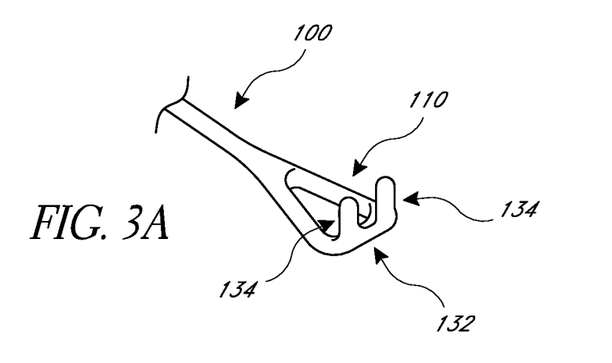
FIG. 3A illustrates an embodiment of the proximal eyelet of the guide needle, which is configured to hold a plug.

With reference to FIG. 3A, there is shown a detailed view of an embodiment of the proximal eyelet 110 at the base of guide needle 100. In this embodiment, the proximal eyelet 110 of guide needle 100 has a recess 132 and prongs 134 configured to receive the plug.

Figure 3B:
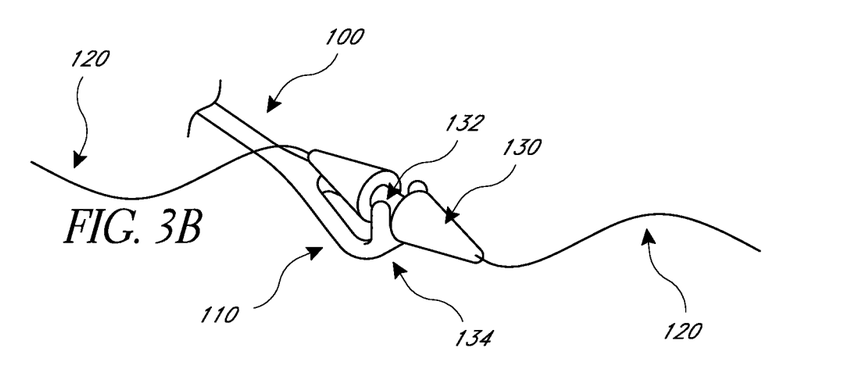
FIG. 3B illustrates an embodiment of the device wherein the plug is secured in the proximal eyelet of the guide needle.

With reference to FIG. 3B, there is shown a detailed view of proximal eyelet 110 at the base of guide needle 100 with plug 130. In this embodiment, the proximal eyelet 110 of guide needle 100 has a recess 132 and prongs 134 configured to receive the plug 130. Suture thread 120 is attached at both ends to plug 130.

Figure 4:
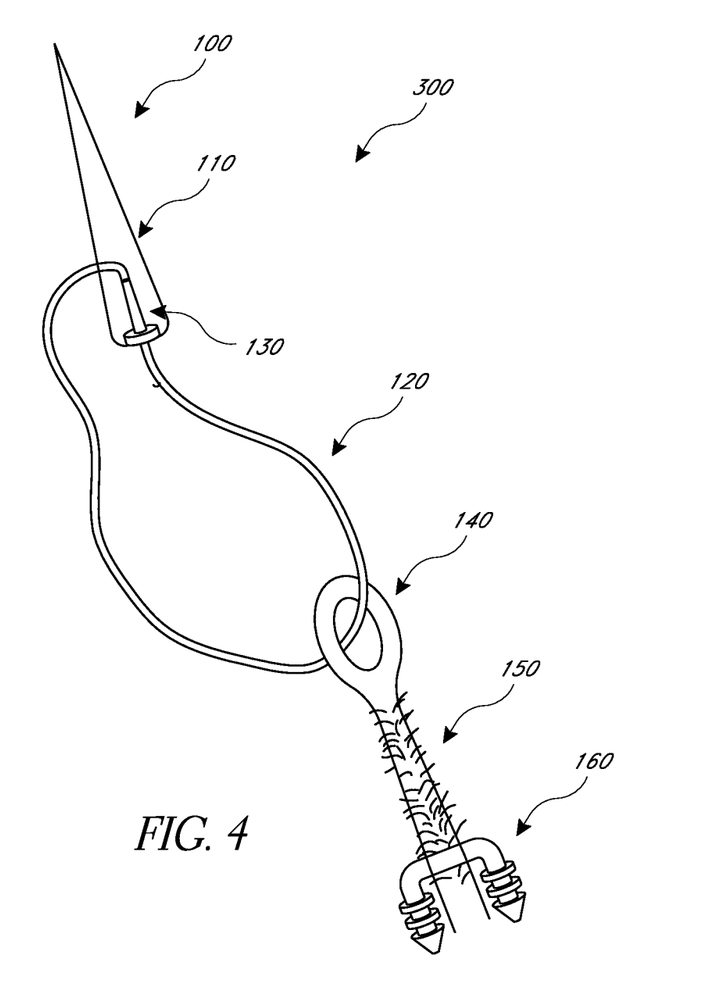
FIG. 4 illustrates an embodiment of the device wherein the plug is pin-shaped.

With reference to FIG. 4, there is shown a detailed view of suture thread 120, attached at both ends to another embodiment of a plug 130. Suture thread 120 goes through the proximal eyelet 110 at the base of guide needle 100 and also through the distal eyelet 140 of elongate member 150.

Figure 5:
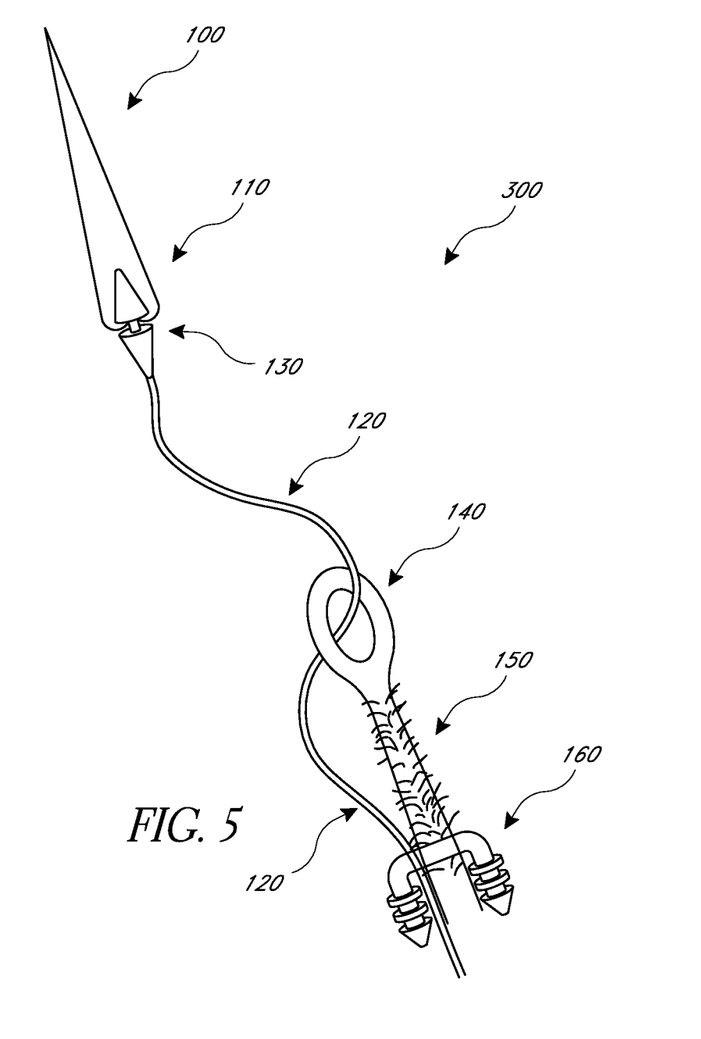
FIG. 5 illustrates an embodiment of the device wherein the plug is attached to the proximal eyelet of the guide needle and the suture thread is a long tail attached to one end of the plug.

With reference to FIG. 5, there is shown a meniscus horn relocation system 300. The meniscus horn relocation system 300 includes a guide needle 100 with proximal eyelet 110, and a suture thread 120 that is attached in the illustrated embodiment at one end to a plug 130. The other end of the suture thread 120 goes through the eyelet 140 of elongate member 150 and bone anchor 160.

Figure 6A:
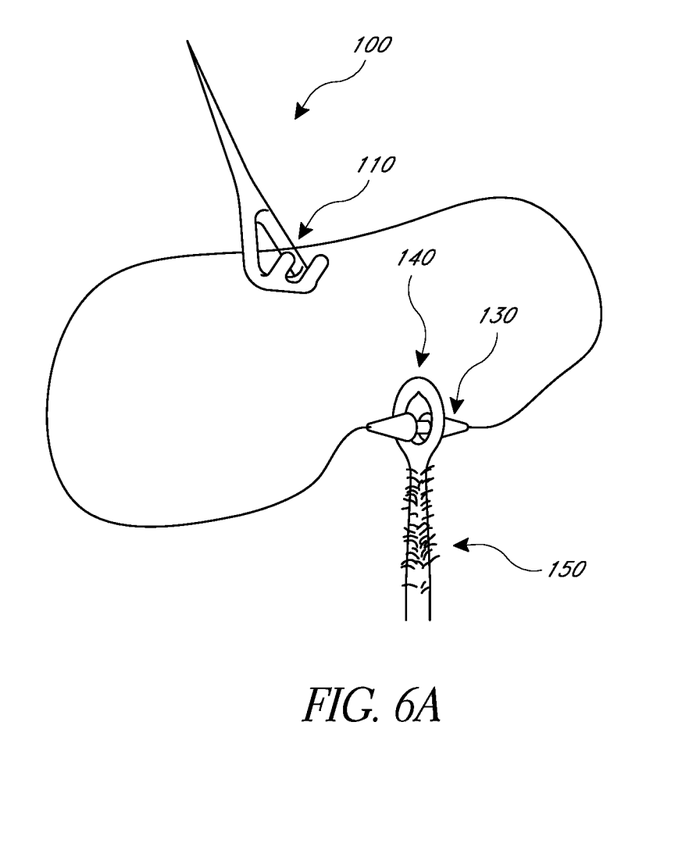
FIG. 6A illustrates an embodiment of the device wherein the eyelet of the elongate member is tear-shaped such that the plug can pass into it, but is secured into the narrow end of the eyelet when the elongate member is drawn back.

With reference to FIG. 6A, there is shown a detailed view of plug 130 passing through eyelet 140 of elongate member 150. In this embodiment, eyelet 140 is tear drop shaped so that plug 130 can pass into it, but when elongate member 150 is drawn back, plug 130 is secured into the narrow end of eyelet 140.

Figure 6B:
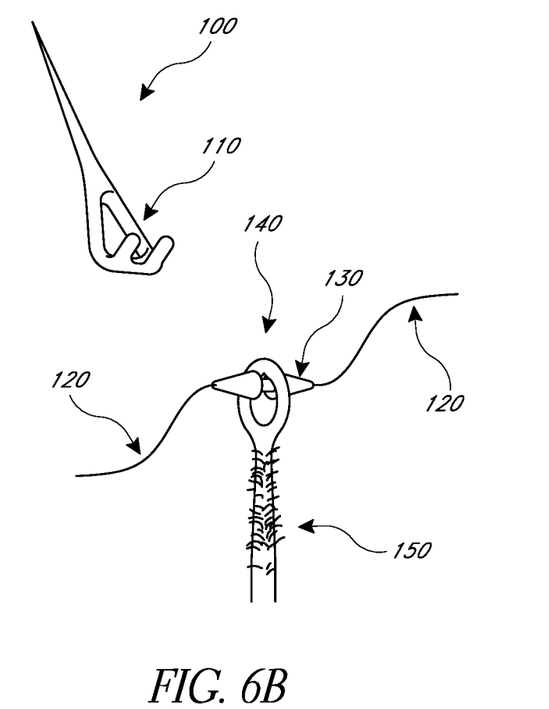
FIG. 6B illustrates an embodiment of the device wherein the plug is secured into the narrow end of the tear-shaped eyelet of the elongate member.

With reference to FIG. 6B, there is shown a detailed view of plug 130 secured into eyelet 140 of elongate member 150. In this embodiment, eyelet 140 is tear drop shaped so that plug 130 can pass into it, but when elongate member 150 is drawn back by cutting and then pulling suture thread 120, plug 130 is secured into the narrow end of eyelet 140.

Figure 7:
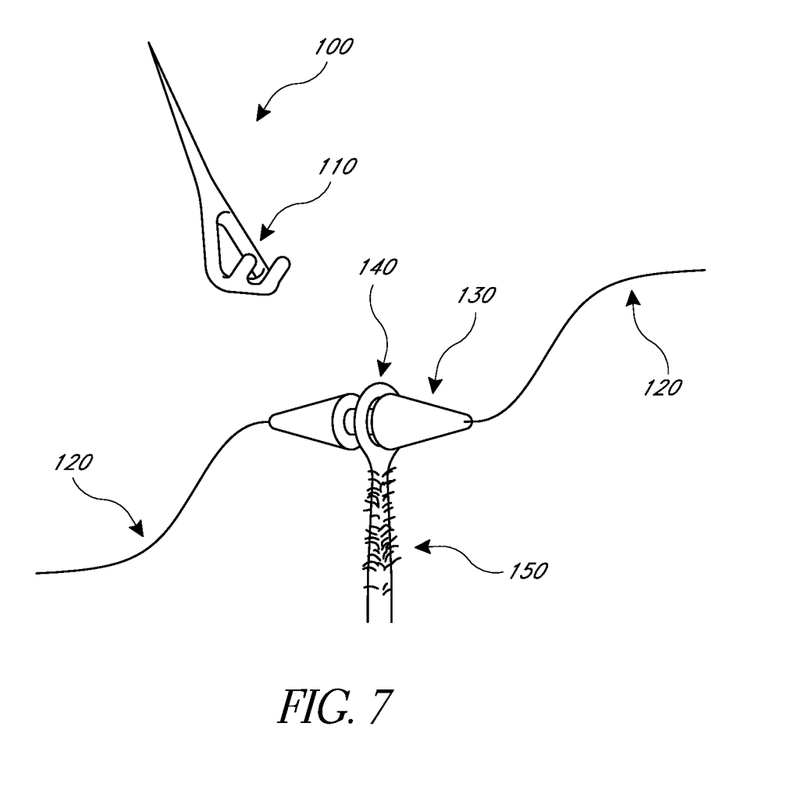
FIG. 7 illustrates an embodiment of the device wherein the plug is secured perpendicularly to the distal eyelet of the elongate member.

With reference to FIG. 7, there is shown a detailed view of plug 130 inside the eyelet 140 of elongate member 150. Suture thread 120 has been cut and is still attached at both ends to plug 130. Suture thread 120 no longer goes through the plug holder 110 at the base of guide needle 100.

Figure 8A:
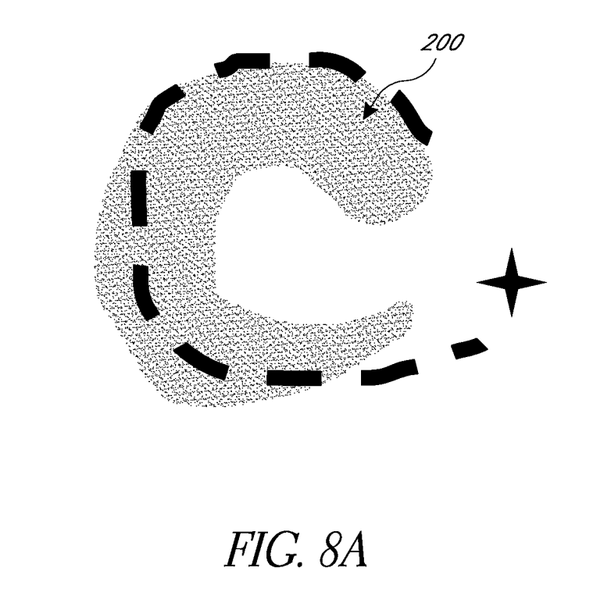
FIG. 8A illustrates the meniscus horn prior to a meniscus horn relocation procedure.

With reference to FIG. 8A, there is shown a meniscus horn 200 within the joint cavity of a knee prior to use of a meniscus horn relocation system. The dotted lines represent the desired final location of the capsular attachment of the meniscus.

Figure 8B:
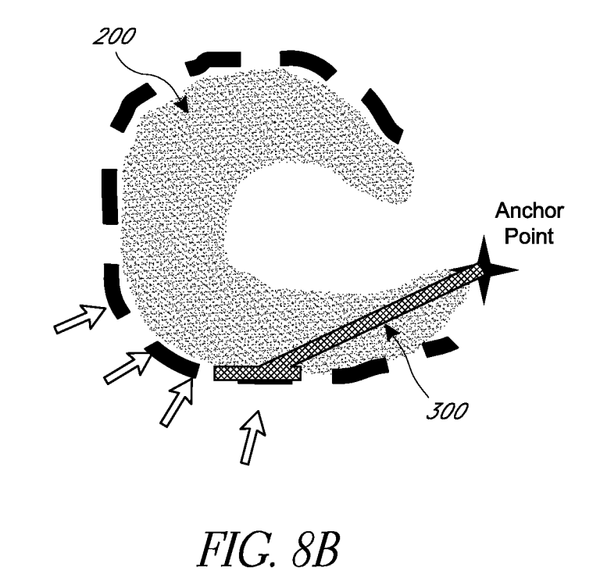
FIG. 8B illustrates the positional shift of the meniscus horn that occurs after a meniscus horn relocation procedure.

With reference to FIG. 8B, there is shown a meniscus horn 200 after relocation with the meniscus horn relocation system 300. The dotted lines represent the desired final location of the capsular attachment of the meniscus.

Figure 9:
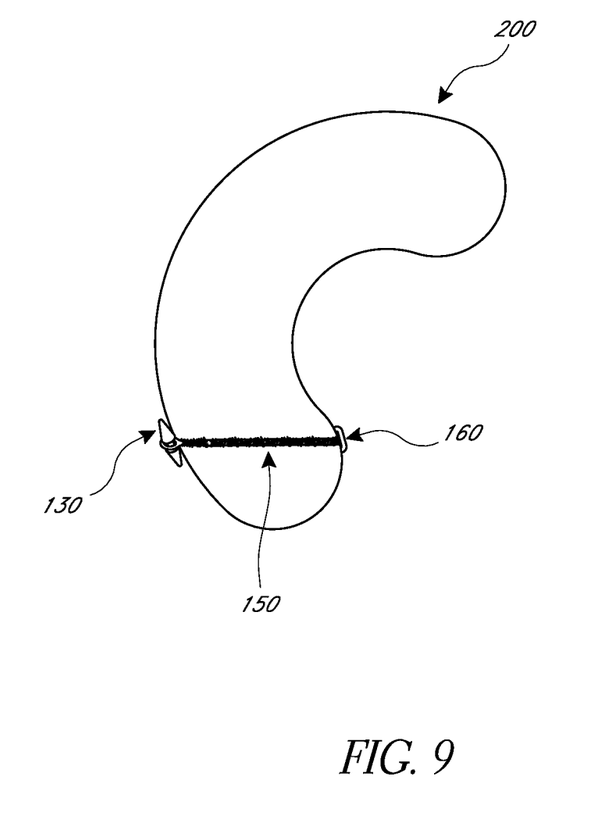
FIG. 9 illustrates an embodiment of the components of the meniscus horn relocation device that remain implanted in the patient.

With reference to FIG. 9, there is shown a detailed view of a meniscus horn 200 after relocation with the meniscus horn relocation system 300. Plug 130 and bone anchor 160 keep the elongate member 150 held in place in meniscus horn 200.

In one embodiment of the meniscus relocation system, the guide needle, suture thread, plug, elongate member, and bone anchor are arranged in series to provide for linear advancement of the system through cartilaginous and other tissues at the site of an arthroscopic meniscus relocation procedure. The guide needle may be used to puncture the meniscus and surrounding tissues, as shown in FIG. 2A. The suture thread may be used to loosely connect the guide needle and elongate member, thereby enabling anterior advancement of the elongate member into the meniscus tissue, as shown in FIG. 2B. The plug may be perpendicularly disposed within the distal eyelet of the elongate member, thereby enabling engagement with the meniscus capsule and securement of the elongate member within the meniscus. The bone anchor may be used to secure the proximal end region of the elongate member to a bony structure of the knee joint. Thus, each component serves an individual function for purposes of an arthroscopic meniscus horn relocation procedure, and some of the components, such as the plug, elongate member, and bone anchor, may remain implanted upon completion of the procedure.

The guide needle generally includes a distal point and proximal eyelet, wherein a longitudinal axis is defined between the distal point and proximal eyelet. The relative size and shape of the guide needle is not limiting, and may vary depending on the anatomical characteristics of the target region of the meniscus relocation procedure. Likewise, the material comprising the guide needle is not limiting, so long as it is sufficiently sturdy to puncture the tissues in and around the meniscus. Similarly, the guide needle may be curved or any other irregular shape to allow passing the needle arthroscopically to be more easily achieved. The guide needle may also have a soft threaded outer portion to allow its rotation to make passing through tough tissues easier.

In some embodiments, the proximal eyelet of the guide needle is configured to be loosely connected to the elongate member via a suture thread loop. In other embodiments, the guide needle further includes a holder configured to reversibly secure a plug, such as that shown in FIG. 3B. Securement of the plug within the holder may enable easier advancement of the plug through meniscus tissues during the relocation procedure, as shown in FIG. 3B. In an alternative embodiment, the plug need not be secured to the guide needle, and may instead trail behind the guide needle during advancement. In yet other embodiments, the plug may include a pin-like structure which may be advanced through the meniscus in parallel with the guide needle.

In some embodiments, the shape and size of the plug is not limiting. In some embodiments, the plug may be any shape and any size so long as the shape and size of the plug and the receiving eyelet on the guide needle are configured to allow the receiving eyelet and the plug to pass through the meniscus capsule with minimum interference during insertion. In another embodiment, the plug may be any shape and any size so long as the receiving eyelet on the guide needle is configured to reversibly hold the plug in an orientation wherein the longitudinal axis of the plug is aligned with the longitudinal axis of the guide needle and the plug is configured to lodge within the distal eyelet of the elongate member in an orientation wherein the longitudinal axis of the plug is substantially perpendicular to the longitudinal axis of the elongate member.

In yet another alternative embodiment, the plug may be fixed onto an eyelet of the guide needle, and may only be released by cutting or breaking the eyelet. In this embodiment, the guide needle and elongate member need not be connected via a suture thread loop, but instead, may be connected by more direct means. Likewise, the shape of the eyelet is not limiting, and may be determined by the relative shape of the plug.

In some embodiments, the elongate member includes a distal eyelet, a body portion, and a proximal end region. In some embodiments, the elongate member includes a flexible polymer material. In other embodiments, the elongate member includes a plurality of flexible polymer materials braided together to form a rope-like structure. In one embodiment, the elongate member is ideally as flexible as possible while still providing the tensile strength necessary to withstand the forces associated with typical knee kinematics.

In some embodiments, the flexible polymer materials may be configured to swell upon exposure to fluids. Thus, the elongate member may swell upon introduction into the meniscus tissue. This may have a bulking effect on the meniscus, causing it to become more prominent, and thereby enhancing the interposition of the meniscus between the femur and tibia at their articular arrangement. Any deformation of the meniscus, by virtue of such a bulking effect, may be counteracted by compressive loads during normal knee joint articulation.

Although the type of flexible polymer material is not limiting, some suitable polymer materials include Nylon and Dacron, but others may suffice as well. Medical grade Dacron is well-known in the prior art and is often used as a biocompatible graft material. However, many alternative materials may be used, so long as they distribute the longitudinal load and are sufficiently flexible so as not to cut into the meniscal tissue during tensile loading.

In further embodiments, the flexible polymer materials may be coated with a biocompatible coating. Alternatively, the flexible polymer material may itself include a biocompatible material. Although the type of biocompatible material is not limiting, some suitable materials include PET and PTFE, among others.

In some embodiments, the body portion of the elongate member further includes a plurality of gripping arms. The gripping arms include hair-like structures protruding radially outward from the elongate member. These protrusions may facilitate engagement between the elongate member and the tissues of the meniscus. For example, hair-like arms of the elongate member may entangle fibrous bands of meniscus tissue so as to provide an internal tensile grip on the meniscus tissue. In some embodiments, a combination of small scale and large scale hairs may optimize such tensile grip. Thus, the elongate member may engage and/or become fixed to the meniscus tissue.

In some embodiments, as with the flexible polymer materials comprising the elongate member, the plurality of gripping arms may include flexible polymer materials such as Nylon or Dacron, and/or may be coated in biocompatible materials such as PET or PTFE. These materials, however, are not limiting, and others may be used. In combination with such biocompatible materials, the flexible polymer materials comprising the plurality of gripping arms may encourage ingrowth of meniscus tissues and/or formation of scar tissue around the elongate member.

For example, blood may enter the interior of the meniscus through the meniscus capsule and thereby provide cells and nutrients in contact with the elongate member. This process may encourage scar tissue adherence to the meniscus, and thereby provide uniform fixation of the elongate member within the meniscus. In addition, uniform fixation results in high surface area contact between the meniscus and elongate member, which may have the effect of minimizing stress localizations when a tensile force is applied to the elongate member.

In some embodiments, the elongate member may be loosely connected to the guide needle via a suture thread loop that may be threaded through the distal eyelet of the elongate member and the proximal eyelet of the guide needle. In an alternative embodiment, the guide needle and elongate member may be connected by more direct means. Thus, the guide needle may be used to pull the elongate member laterally into the meniscus.

The shape and size of the distal eyelet of the elongate member is not limiting. For example, in some embodiments, the eyelet may be generally circular, while in other embodiments it may be a teardrop shape. In some embodiments, the shape and size of the eyelet may be determined by the relative shape and size of the plug. Generally, the plug must be capable of being inserted through the distal eyelet, perpendicular to the elongate member, such as that shown in FIG. 7. Thus, the plug may be used to fix the longitudinal position of the elongate member within the meniscus.

In some embodiments, the plug includes a pliant material. However, the material of the plug is not limiting and may include radio-opaque elements to assist in post-operative imaging. Likewise, the shape of the plug is not limiting, so long as it may be secured at the distal end of the elongate member in a generally perpendicular orientation. In some embodiments, the plug includes a generally cylindrical shape. In other embodiments, the plug includes a double-cone shape, such as that shown in FIGS. 1, 2A, 2B, 3B, 5, 6A, 6B, and 7. In these and other embodiments, the plug further includes a ring cut-out, whereby the plug may more easily engage the distal eyelet of the elongate member, such as in FIG. 7. In yet other embodiments, the plug includes a pin-like structure, which may be inserted substantially through the distal eyelet such that the head of the pin engages the distal eyelet.

In some embodiments, the bone anchor may be used to secure the device to a bony structure in the body of a patient. Bone anchors are well-known in the field of arthroscopic surgery, and any bone anchor suitable for securing the proximal end region of the elongate member may be used. Thus, the specific type of bone anchor and the specific location of securement may vary depending on the needs of the patient or operating physician. The proximal anchoring of the elongate member may also be to non-bony structures, for example, the posterior or anterior cruciate ligament, to provide a more kinematically dynamic displacement of the posterior aspect of the meniscus during movement of the knee. In this embodiment, the anchoring system will be suitable for soft tissue attachment.

In general, the following steps may be used to relocate a meniscus using the disclosed system.

As shown in FIG. 2A, the guide needle arthroscopically enters the joint cavity and enters the meniscus obliquely at the posterior meniscal horn that is to be relocated. In some embodiments, the entry point is in the mid substance of the meniscus at the median edge of the posterior horn. However, the points of entry and exit of the device in the meniscus may be determined by the operating surgeon.

The guide needle is then pushed through the meniscus, through the meniscus capsule and out through the skin. This causes the elongate member, which is attached to the guide needle via the suture thread or other more direct means, to be introduced into the meniscus body and is pulled until the distal eyelet of the elongate member reaches the meniscus capsule, as shown in FIG. 2B. For example, having the guide needle pass through the skin may then allow the surgeon to feel, through the increased tension, the distal eyelet of the elongate member advance through the outer capsule on the meniscus. Alternatively, the surgeon may visualize this event by virtue of a tenting effect on the meniscus capsule superficial to the meniscal edge. A further option is to use intra-operative imaging, through image intensifier radiography, ultrasound or another modality, to image the position of the implant. In the event that the needle is drawn too far and the elongate member goes past the distal edge of the meniscus capsule, then a tension may be applied to the proximal end region of the elongate member, thereby pulling the elongate member proximally into the desired position.

When the guide needle has penetrated the skin and the eyelet of the elongate member has pushed through the capsule of the meniscus, the suture thread above may then be cut distal to the plug. Pulling on the loose end of the suture thread, proximal to the plug, enables the plug to be pulled through the distal eyelet of the elongate member, as shown in FIG. 7. The plug, which is now positioned perpendicular to the elongate member, is wider than the hole created by the guide needle in the tough meniscal capsule tissue. The plug ensures that the elongate member remains in a fixed position with respect to the meniscus capsule at its distal end. Thus, the position of the plug abutting the outer surface of the meniscus capsule enables the application of median tensile forces to the proximal end region of the elongate member.

A tensile force may then be applied to the proximal end region of the elongate member, thereby causing physical relocation of the meniscus horn within the knee joint. In some embodiments, tension may be applied only after the knee joint is loaded. This may be accomplished by applying force to the proximal end region of the elongate member until the meniscus is snug within the joint. Next, the knee joint is relaxed, and the proximal end region of the elongate member may then be pulled an additional length to relocate the meniscus to the desired location, as shown in FIGS. 8A and 8B.

The additional length used to relocate the meniscus may vary depending on the anatomy of the patient or the requirements of the operating physician. In one embodiment, an additional length of 2 mm may be sufficient to relocate the meniscus, however, this length is not limiting. The additional length may also be determined by measuring the load required to create the consequent displacement under different loading conditions of the joint and flexion angles.

Next, a bone anchor may be used to anchor the proximal end region of the elongate member into a bony structure adjacent to the knee joint. After fixation, any excess length of the elongate member or suture thread may then be cut off and removed. Alternatively, a soft tissue anchor may be used to secure the implant to a non-bony structure within the knee.

The specific anchor location may vary depending on the requirements of a given procedure. Thus, any suitable location may be used. In one embodiment, the anchoring step is performed on the tibial intercondylar eminence, which is located away from articular cartilage in the knee joint, and thus away from both the blood supply area of the meniscus and the cruciate ligaments. Such anchoring techniques have been demonstrated in the context of ACL fixation procedures, and have been shown to not result in adverse effects, such as tissue necrosis.

In some embodiments, there may be a post-procedural risk of the plug pulling through the meniscus capsule and into the meniscus. This may be particularly evident during normal activity of the knee joint, such as, for example, when the meniscus is squeezed under a load while the patient walks. The relative risk of plug displacement may be determined by the choice of polymer material used for the elongate member. For example, the choice of polymer will determine the relative elasticity of the elongate member, as well as the maximum tension threshold of the implanted device. The specific dimensions and materials for a given embodiment of the present invention may vary depending on a number of factors, such as the relative condition, size, shape, and strength, among other factors, of the patient.

In patients whose meniscus is displaced due to laxity in the meniscus capsule caused by wear on the knee, the relocation of the posterior meniscal horn to a new point on the tibia may have the effect of pulling the meniscus pad into areas in the joint cavity where the femur and tibia meet during normal weight bearing activities.

The aim of the above procedure is to restore alignment of the of the knee joint, at least partially, by including the meniscus in the articulation of the joint. This may ensure that no significant disruption to normal knee kinematics will occur during subsequent activity of the joint. Furthermore, the cushioning and lubricating effects of the meniscus pad may have the effect of counteracting the pain associated with osteoarthritic bony surfaces in a damaged or worn knee joint.

In one application, the present invention is designed to delay the progression of osteoarthritis rather than reverse it. Subsequently cutting the elongate member from the bone anchor may thus eliminate the tensioning effect of the invention without the need to extricate all of the implanted materials. Likewise, removal of the implanted portions of the system may be achieved during subsequent total knee replacement, or other invasive surgery.

What is claimed is:

1. A device comprising:
   a guide needle comprising a proximal eyelet;
   an elongate member comprising: a distal eyelet and an elongate body portion comprising a plurality of gripping arms; and
   a suture thread comprising a first end threaded through the proximal eyelet of the guide needle and a second end threaded through the distal eyelet of the elongate member, wherein the first and second ends of the suture thread are coupled to opposing ends of a plug, thereby forming a closed loop that flexibly couples the guide needle to the elongate member, wherein the plug comprises a generally double-cone shape having a maximum radius adjacent to a center of the plug, and wherein the center of the plug is defined by a circumference configured to mate with an inner circumference of the distal eyelet of the elongate member.

2. The device of claim 1, wherein the proximal eyelet comprises a holder configured to hold the plug.

3. The device of claim 2, wherein the holder comprises a receiving structure configured to reversibly hold the plug in an orientation wherein a longitudinal axis of the plug is aligned with a longitudinal axis of the guide needle.

4. The device of claim 3, wherein the receiving structure comprises one or more prongs extending from the proximal eyelet of the guide needle.

5. The device of claim 1, wherein the plug has an elongate shape comprising a longitudinal axis.

6. The device of claim 1, wherein the plug is configured to lodge within the distal eyelet of the elongate member in an orientation wherein a longitudinal axis of the plug is substantially perpendicular to a longitudinal axis of the elongate member.

7. The device of claim 1, wherein at least the elongate body portion of the elongate member comprises a polymer material.

8. The device of claim 7, wherein the polymer material is configured to swell upon exposure to fluids.

9. The device of claim 7, wherein the polymer material is Nylon or Dacron.

10. The device of claim 7, wherein the polymer material is coated with a biocompatible material.

11. The device of claim 10, wherein the biocompatible material is configured to swell upon exposure to fluids.

12. The device of claim 10, wherein the biocompatible material comprises PET or PTFE.

13. The device of claim 1, wherein at least the elongate body portion of the elongate member comprises a plurality of polymer materials configured to form a braid.

14. The device of claim 1, wherein the plurality of gripping arms comprises a plurality of threads protruding radially outward from the elongate body portion, wherein the plurality of threads are configured to engage fibrous tissue.

15. The device of claim 14, wherein the plurality of threads comprises a mixture of hooks comprising at least two different hook lengths.

16. The device of claim 14, wherein the plurality of threads comprises a plurality of hair-like filaments.

17. The device of claim 14, wherein the plurality of threads is configured to encourage scar tissue formation in the engaged fibrous tissue.

18. The device of claim 14, wherein the plurality of threads is configured to swell upon exposure to fluids.

19. A device comprising:
a guide needle comprising a proximal eyelet;
an elongate member comprising: a distal eyelet and an elongate body portion comprising a plurality of gripping arms; and
a suture thread comprising a first end threaded through the proximal eyelet of the guide needle and a second end threaded through the distal eyelet of the elongate member, wherein the first and second ends of the suture thread are coupled to opposing ends of a plug, thereby forming a closed loop that flexibly couples the guide needle to the elongate member, wherein the plurality of gripping arms comprises a plurality of threads protruding radially outward from the elongate body portion, wherein the plurality of threads are configured to engage fibrous tissue, and wherein the plurality of threads comprises a mixture of hooks comprising at least two different hook lengths.

20. The device of claim 19, wherein the proximal eyelet comprises a holder configured to hold the plug.

21. The device of claim 20, wherein the holder comprises a receiving structure configured to reversibly hold the plug in an orientation wherein a longitudinal axis of the plug is aligned with a longitudinal axis of the guide needle.

22. The device of claim 21, wherein the receiving structure comprises one or more prongs extending from the proximal eyelet of the guide needle.

23. The device of claim 19, wherein the plug has an elongate shape comprising a longitudinal axis.

* * * * *